United States Patent [19]

Suzuki et al.

[11] Patent Number: 4,827,056
[45] Date of Patent: May 2, 1989

[54] PROCESS FOR PREPARING CHLORINATED OLEFINS

[75] Inventors: Shigeaki Suzuki; Toshiki Mori; Takashi Onishi; Yoshiji Fujita, all of Kurashiki, Japan

[73] Assignee: Kuraray Company Ltd., Kurashiki, Japan

[21] Appl. No.: 164,917

[22] Filed: Mar. 7, 1988

[30] Foreign Application Priority Data

Mar. 17, 1987 [JP] Japan .................. 62-63418

[51] Int. Cl.$^4$ .................. C07C 21/04
[52] U.S. Cl. .................. 570/189
[58] Field of Search .................. 570/189

[56] References Cited

FOREIGN PATENT DOCUMENTS 0067439 4/1985 Japan .................. 570/189

Primary Examiner—Werren B. Lone
Attorney, Agent, or Firm—Oblon, Fisher, Spivak, McClelland & Maier

[57] ABSTRACT

Chlorinated olefins of general formula (I),

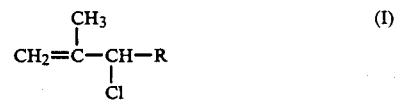

wherein R is an alkyl, aralkyl, or alkenyl group substituted or not substituted by a lower acyloxy, lower alkyloxy, alkenyloxy or benzyloxy group, are prepared by the reaction of hypochlorous acid, generated by the reaction of sodium hypochlorite with a strong mineral acid, and olefins of general formula (II),

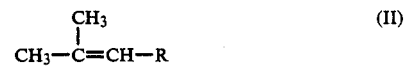

wherein R is the same as defined above, in a two-phase system of water phase and organic solvent phase, not being miscible with water.

11 Claims, No Drawings

PROCESS FOR PREPARING CHLORINATED OLEFINS

BACKGROUND OF THE INVENTION (1) Field of the Invention

This invention relates to a process for the preparation of chlorinated olefins of the following general formula (I),

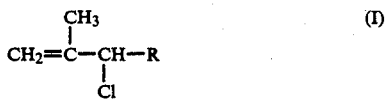

wherein R is an alkyl, aralkyl or alkenyl group substituted or not substituted by a lower acyloxy, lower alkyloxy, alkenyloxy or benzyloxy group.

The chlorinated olefins produced by the method of this invention shown in the general formula (I) are utilized as intermediates for the synthesis of various terpenoids which are in use of perfumes, feed additives, medicines and the like. [See ① Japanese Patent Laid-open No. 59-106434, ② Japanese Patent Laid-open No. 60-136549, ③ Japaneses Patent Laid-open No. 61-194047, ④ Bull. Chem. Soc. Japan, 59, 3287 (1986).]

(2) Description of the Related Art

It has been reported that chlorinated olefins of general formula (I) can be prepared by the chlorination of the olefins shown as the general formula (II) with one of the following chlorinating agents,

wherein, R is the same as defined in the general formula (I).

① Diaryl diselenide and N-chlorosuccinimide [see J. Org. Chem., 44, 4204 (1979)].

② Hypochlorous acid prepared by the reaction of calcium hypochlorite and dry ice [see Tetrahedron Lett., 21, 441 (1980)].

③ Hypochlorous acid or oxygen dichloride prepared by the electrolytic oxidation of chloride ion [see Tetrahedron Lett., 22, 2291 (1981)].

④ t-Butyl hypochlorite [see Chem. Lett., 141 (1982)].

⑤ Trichloroisocyanuric acid and its derivatives [see Japanese Patent Laid-open No. 58-52231].

⑥ Sulfuryl chloride [see Chem. Pharm. Bull., 32, 3952 (1984)].

⑦ Oxygen dichloride [see Chem. Lett., 877 (1984)].

The above mentioned conventional methods of preparing chlorinated olefins have the following problems.

Method ①: Both diaryl diselenide and N-chlorosuccinimide are expensive.

Method ②: Difficulty in work-up procedure because of low solubility of calcium carbonate in water.

Method ③: Not in general because of the need of electrolytic reaction apparatus.

Method ④: Unsuitable for the preparation in large quantity because of the unstability and expensiveness of t-butyl hypochlorite.

Method ⑤: Difficulty in work-up procedure because of low solubility of generated cyanuric acid in organic solvents.

Method ⑥: Necessity of keeping the very low temperature at the reaction is not suitable for a commercial scale production.

Method ⑦: Oxygen dichloride is very dangerous to handle in large quantity because of its explosiveness.

As mentioned above, the conventional methods of preparing chlorinated olefins are difficult to adopt in a commercial scale production because of the problems, such as (i) expensive reagents, (ii) difficulty in work-up procedure, (iii) unstable reagents which are dangerous to handle in large quantity, (iv) necessity of special reaction apparatus, (v) necessity of special reaction condition.

Accordingly, an object of this invention is to provide a process for preparing chlorinated olefins of general formula (I) in commercial scale dissolving the above mentioned problems.

Other objects, features and advantages of this invention will become apparent from the following description.

SUMMARY OF THE INVENTION

According to the present invention, the above mentioned objects are attained by the reaction of olefin of general formula (II) with hypochlorous acid generated by the reaction of sodium hypochlorite with a strong mineral acid in a two-phase system of water-immiscible organic solvent and water.

Present inventors have conducted an intensive study on the manufacturing method of chlorinated olefins of general formula (I) suitable for a commercial production paying the attention to hypochlorous acid among the above mentioned conventional reagents from the standpoint of reagent cost, and found that the operability of after-treatement was surprisingly improved by the use of sodium hypochlorite instead of calcium hypochlorite in the above mentioned conventional ② method. Furthermore, the use of a strong mineral acid instead of dry ice in the above mentioned conventional ② method surprisingly decreases by-products and increases the yield of desired chlorinated olefins of general formula (I). The invention was accomplished by the integration of these findings.

DESCRIPTION OF THE PREFERRED EMBODIMENTS

Referring to the above mentioned general formula, R is an alkyl, aralkyl or alkenyl group substituted or not substituted by a lower acyloxy, lower alkyloxy, alkenyloxy or benzyloxy group.

Examples of lower acyloxy group are formyloxy, acetoxy, propionyloxy, butyryloxy group. Examples of lower alkyloxy group are methoxy, ethoxy, propoxy, butoxy, ethylene dioxy group. Examples of alkenyloxy group are 3-methyl-2-butene-1-yl-oxy, 1,1-dimethyl-2-propene-1-yl-oxy group.

Examples of alkyl group are straight or branched having carbon number from 1 to about 20 such as n-pentyl, n-nonyl, 3-methylbutyl and the like and also can be substituted by the above mentioned lower acyloxy, alkyloxy, alkenyloxy or benzyloxy group, such as 1-methoxy-pentyl, 5-acetoxy-3-methylpentyl, 5-benzyloxy-3-methyl-pentyl, 3-acetoxy-3-3-methylbutyl, acetoxymethyl, benzyloxy-methyl, dimethoxymethyl, 3-methyl-2-butene-1-yl-oxymethyl, 1,1-dimethyl-2-propene-1-yl-oxymethyl group and the like.

Examples of aralkyl group are phenylmethyl, p-t-butylphenylmethyl group and the like, and also can be substituted by the above mentioned lower acyloxy, lower alkyloxy, alkenyloxy or benzyloxy group, such as 2,5-diacetoxy-3,4,6-trimethylphenylmethyl, 2,6-diacetoxy-3,4-dimethoxy-6-methylphenylmethyl group and the like.

Examples of alkenyl group are 3-methylene-4-penten-1-yl, 7-methylene-3-methyl-8-nonen-1-yl, 3-methyl-2-buten-1-yl group and the like, and also can be substituted by the above mentioned lower acyloxy, lower alkyloxy, alkenyloxy or benzyloxy group, such as 5-acetoxy-3-methyl-3-penten-1-yl, 5-benzyloxy-3-methyl-3-penten-1-yl, 5,5-dimethoxy-3-methyl-3-penten-1-yl, 9-acetoxy-3,7-dimethyl-3,7-nonadien-1-yl, 9-benzyloxy-3,7-dimethyl-3,7-nonadien-1-yl, 13-acetoxy-3,7,11-trimethyl-3,7,11-tridecatrien-1-yl, 7,7-ethylenedioxy-3-methyl-3-octen-1-yl and the like.

According to the invention, 1-lower acyloxy-6-chloro-3,7-dimethyl-2,7-octadiene obtained by the reaction of olefins of general formula (II) having R of 5-lower acyloxy-3-methyl-3-penten-1-yl group are useful as intermediates for the synthesis of vitamin A or its acetate.

The preparing method of chlorinated olefins of general formula (I) of the invention is described in the following.

The reaction according to the invention is conducted by the addition of a strong mineral acid to a two-phase system of aqueous phase dissolving sodium hypochlorite and organic solvent phase dissolving olefin of general formula (II). Hypochlorous acid is generated in situ by the reaction of sodium hypochlorite and a strong mineral acid.

A commercially available sodium hypochlorite aqueous solution having 8.5–13.5% of available chlorine concentration can be used. A preferable amount of sodium hypochlorite used is from about 0.8 to 1.5 moles per mole of olefins of general formula (II).

Preferable examples of organic solvent dissolving olefins of general formula (II) are hydrocarbons, such as hexane, benzene, toluene and the like, halogenated hydrocarbons, such as dichloromethane, 1,2-dichloroethane and the like. A preferable amount of organic solvent used is from about 0.5 to 50 ml per g of olefins of general formula (II).

Preferable examples of strong mineral acid used for the generation of hypochlorous acid from sodium hypochlorite are hydrochloric, sulfuric, nitric acid and the like, and more preferables are hydrochloric and sulfuric acid. It is convenient to use as an aqueous solution of strong mineral acid at a proper concentration. Concentrated hydrochloric acid, or diluted hydrochloric acid diluted until about 0.1N with water; concentrated sulfuric acid, or diluted sulfuric acid diluted until 0.1N with water; or concentrated nitric acid, or diluted nitric acid diluted until about 0.1N with water can be used. A preferable amount of strong mineral acid is from about 0.9 to 1.2 equivalents per mole of sodium hypochlorite. A preferable reaction temperature is from about 0° to 25° C.

The thus obtained chlorinated olefin of general formula (I) is separated and purified from the reaction mixture in the following manner. The aqueous phase separated from the organic solvent phase is washed with dichloromethane, hexane, toluene, isopropyl ether or ethyl acetate and added to the separated organic solvent phase. The combined solution is washed successively with sodium sulfite aqueous solution and sodium hydrogen carbonate aqueous solution, and then removal of the solvent by distillation gives crude chlorinated olefin of general formula (I). Objective highly purified chlorinated olefins of general formula (I) are obtained by distillation, column chromatography and the like.

As described above, the process of this invention, (i) using sodium hypochlorite and a strong mineral acid as reagents of inexpensive and stable enough for handling in large quantity in commercial production (ii) the work-up procedure being very easy because the reaction product of hypochlorous acid generation dissolves well in water, (iii) not requiring of special apparatus and reaction condition, is an excellent way dissolving problems of conventional methods, increasing the yield of desired chlorinated olefins of general formula (I), and being advantageous for commercial production.

EXAMPLES

The present invention will now be described with reference to the following examples.

EXAMPLE 1

The synthesis of 6-chloro-3,7-dimethyl-2,7-octadienyl acetate.

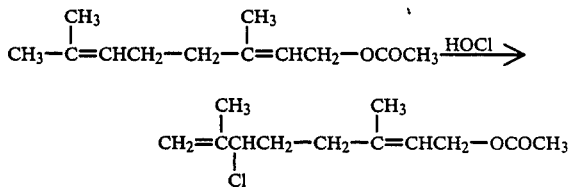

3,7-dimethyl-2,6-octadienyl acetate 20.00 g (102 mmol), dichloromethane 100 ml, and sodium hypochlorite aqueous solution (12.58%) 62.20 g (sodium hypochlorite 105 mmol) were placed in a flask. To the mixture, hydrochloric acid aqueous solution (1.18N) 95.0 ml (112 mol) was added in dropwise over a period of 45 minutes below 10° C. The mixture was stirred for further 15 minutes at 4° C. To the mixture, 100 ml of 10% sodium thiosulfate aqueous solution and 100 ml of 10% sodium carbonate aqueous solution were added successively and stirred for five minutes, and then the organic layer was separated. The aqueous layer was extracted with 100 ml of dichloromethane, and the extract was added to the organic layer. The organic solvent was distilled off under reduced pressure to give 26.32 g of colorless liquid.

The crude product was found 78.6% purity of 6-chloro-3,7-dimethyl-2,7-octadienyl acetate by gas chromatography using n-tridecane as the internal standard. Yield was 88%. 6-chloro-7-hydroxy-3,7-dimethyl-2-octenyl acetate, a main by-product of chlorination reaction was found to 6.0% of relative peak area ratio.

The analytical data of 6-chloro-3,7-dimethyl-octadienyl acetate purified by a column chromatography packed with silica gel [eluent: hexane/ethyl acetate (volume ratio)=1/9–⅓] are as follows.

NMR (Hexamethyldisiloxane/CDCl$_3$) δ: 1.63 (s, 3H), 1.75 (s, 3H), 2.00 (s, 7H), 4.27 (m, 1H), 4.53 (d, J=7 Hz, 2H), 4.85 (m, 1H), 4.97 (s, 1H), 5.33 (t, J=7 Hz, 1H).

IR (Film) ν: 1725 (C=O), 895 (CH$_2$=C)cm$^{-1}$.

FI-MS m/e(Relative intensity): 232 (18, M$^+$), 230 (100, M$^+$), 194 (58, M$^+$ —HCl).

EXAMPLE 2-4

The reaction and work-up procedures of Example 1 were repeated except that the solvents shown in Table 1 were used in lieu of 100 ml of dichloromethane to give 6-chloro-3,7-dimethyl-2,7-octadienyl acetate. The yield of the product and the relative peak area ratio of 6-chloro-7-hydroxy-3,7-dimethyl-2-octenyl acetate, a main by-product are shown in Table 1.

TABLE 1

| Example No. | Solvent Name | Amount (ml) | Amount of NaOCl Aqueous Solution (g) | Yield of 6-chloro-3,7-dimethyl-2,7-octadienyl acetate (%) | Relative Peak Area Ratio of 6-chloro-7-hydroxy-3,7-dimethyl-2-octenyl acetate (%) |
|---|---|---|---|---|---|
| 2 | 1,2-dichloroethane | 100 | 63.50 | 87 | 5.6 |
| 3 | toluene | 100 | 69.55 | 88 | 4.8 |
| 4 | benzene | 100 | 69.50 | 87 | 5.0 |

EXAMPLE 5-8

The reaction and work-up procedures of Example 1 were repeated except that the strong mineral acids shown in Table 2 were used in lieu of 95.0 ml (112 mmol) of hydrochloric aqueous solution (1.18N) to give 6-chloro-3,7-dimethyl-2,7-octadienyl acetate. The yield of the product and the relative peak area ratio of 6-chloro-7-hydroxy-3,7-dimethyl-2-octenyl acetate, a main by-product are shown in Table 2.

TABLE 2

| Example No. | Strong Mineral Acid Name | Conc. (N) | Amount (ml) | Yield of 6-chloro-3,7-dimethyl-2,7-octadienyl acetate (%) | Relative Peak Area Ratio of 6-chloro-7-hydroxy-3,7-dimethyl-2-octenyl acetate (%) |
|---|---|---|---|---|---|
| 5 | HCl | 2.01 | 55.8 | 88 | 6.3 |
| 6 | HCl | 3.10 | 36.2 | 88 | 6.2 |
| 7 | HCl | 4.05 | 27.7 | 87 | 6.2 |
| 8 | H$_2$SO$_4$ | 1.05 | 106.8 | 87 | 5.4 |

COMPARATIVE EXAMPLE 1

3,7-dimethyl-2,6-octadienyl acetate 20.00 g (102 mmol), dichloromethane 100 ml and sodium hypochlorite aqueous solutin (12.58%) 62.20 g were placed in a flask. To the mixture, a small pieces of solid dry ice were gradually added, keeping the temperature of content 10° C. or less cooled by ice bath. After an exotherm was no longer observed upon addition of solid dry ice, the reaction mixture was stirred for 15 minutes at 4° C. To the mixture, 100 ml of a 10% sodium thiosulfate aqueous solution and 100 ml of a 10% sodium carbonate were added successively and stirred for 5 minutes, and then the organic layer was separated. The aqueous layer was extracted with 100 ml of dichloromethane, and the extract was added to the organic layer. The organic solvent was distilled off under reduced pressure, to give 26.10 g of colorless liquid. The crude product was found 73.9% purity of 6-chloro-3,7-dimethyl-2,7-octadienyl acetate by gas chromatography using n-tridecane as the internal standard. Yield was 82%. 6-chloro-7-hydroxy-3,7-dimethyl-2-octenyl acetate, a main by-product of chlorination reaction was found to have 9.6% of relative peak area ratio.

EXAMPLES 9-18

The reaction and work-up procedures of Example 1 were repeated except that the olefins of general formula (II) shown in Table 3 were used in lieu of 20.00 g of 3,7-dimethyl-2,6-octadienyl acetate to give corresponding chlorinated olefins of general formula (I) as shown in Table 3. The reaction products were purified by distillation or column chromatography packed with silica gel, and identified by the comparison to the standard compounds prepared by conventional methods.

TABLE 3

| Example No. | Olefin R | Amount (g) | Yield of Chlorinated Olefin (%) |
|---|---|---|---|
| 9 | CH$_3$ CH$_2$ CH$_2$ CH$_2$— | 12.84 | 87* |
| 10 | C$_6$H$_5$ CH$_2$ OCH$_2$— | 17.98 | 92* |
| 11 | CH$_3$ COOCH$_2$— | 13.03 | 30* |
| 12 | CH$_3$ CH$_2$ CH$_2$ CH$_2$ CH(OCH$_3$)— | 15.90 | 85* |
| 13 | (CH$_3$ O)CH— | 13.26 | 47* |
| 14 | (CH$_3$)$_2$ C=CHCH$_2$ OCH$_2$— | 15.71 | 71* |
| 15 | CH$_2$=CHC(CH$_3$)$_2$ OCH$_2$— | 15.68 | 77* |
| 16 | (CH$_3$)$_2$ C=CHCH$_2$— | 12.65 | 68* |
| 17 | CH$_3$ COOCH$_2$ CH=C(CH$_3$)CH$_2$ CH$_2$— CH=C(CH$_3$)CH$_2$ CH$_2$— | 26.90 | 65** |
| 18 | C$_6$H$_5$ CH$_2$— | 14.88 | 77* |

*Purified by distillation.
**Purified by column chromatography.

What is claimed is:

1. A process for preparing a chlorinated olefin of the formula:

(I)

wherein R is an alkyl, phenylalkyl, or alkenyl group, or an alkyl, phenylalkyl or alkenyl group substituted by lower acyloxy, lower alkyloxy, alkenyloxy or benzyloxy, comprising:

reacting an olefin of the formula:

(II)

wherein R is the same as defined above, with hypochlorous acid generated by the reaction of sodium hypochlorite with a strong mineral acid, in a two-phase system of water and an organic solvent which is not miscible with water.

2. The process of claim 1, wherein the amount of said sodium hypochlorite ranges from about 0.8 to 1.5 mole per mole of said olefin reactant.

3. The process of claim 1, wherein the amount of said strong mineral acid ranges from about 0.9 to 1.2 equivalent per mole of said sodium hypochlorite.

4. The process of claim 1, wherein said chlorination reaction is conducted at a temperature ranging from 0° to 25° C.

5. The process of claim 1, wherein said strong mineral acid is hydrochloric acid, sulfuric acid or nitric acid.

6. The process of claim 1, wherein said organic solvent is a hydrocarbon or a halogenated hydrocarbon.

7. The process of claim 6, wherein said hydrocarbon solvent is hexane, benzene or toluene.

8. The process of claim 1, wherein said alkyl group is a straight or branched chain hydrocarbon having from 1 to 20 carbon atoms; said phenylalkyl group is phenylmethyl or p-t-butylphenylmethyl; and said alkenyl group is 3-methylene-4-penten-1-yl, 7-methylene-3-methyl-8-nonen-1-yl or 3-methyl-2-buten-1-yl.

9. The process of claim 1, wherein said lower acyloxy group is formyloxy, acetoxy, propionyloxy or butyryloxy; said lower alkyloxy group is methoxy, ethoxy, propoxy, butoxy, or ethylenedioxy; and said alkenyloxy group is 3-methyl-2-buten-1-yloxy or 1,1-dimethyl-2-propen-1-yloxy.

10. The process of claim 5, wherein said strong mineral acid is hydrochloric or sulfuric acid.

11. The process of claim 1, wherein group R of said olefin reactant is 5-loweracyloxy-3-methyl-3-penten-1-yl.

* * * * *